(12) United States Patent
Cragg

(10) Patent No.: US 8,037,773 B2
(45) Date of Patent: Oct. 18, 2011

(54) METHOD OF CONSIDERING THE DYNAMIC BEHAVIOR OF A MOVABLE MEMBER OF A MACHINE FOR PERFORMING A WHEEL FATIGUE TEST

(75) Inventor: Stephen R. Cragg, Shrosphire (GB)

(73) Assignee: GKN Land Systems Limited, Telford (GB)

( * ) Notice: Subject to any disclaimer, the term of this patent is extended or adjusted under 35 U.S.C. 154(b) by 203 days.

(21) Appl. No.: 12/474,839

(22) Filed: May 29, 2009

(65) Prior Publication Data

US 2010/0024565 A1 Feb. 4, 2010

(30) Foreign Application Priority Data

Jul. 31, 2008 (GB) .................................. 0814037.8

(51) Int. Cl.
*G01N 3/32* (2006.01)
(52) U.S. Cl. ............................................ 73/812; 73/760
(58) Field of Classification Search ......... 73/146–146.8, 73/760–860
See application file for complete search history.

(56) References Cited

U.S. PATENT DOCUMENTS

| | | | | |
|---|---|---|---|---|
| 2,953,018 A | * | 9/1960 | Volmer ............................ | 73/812 |
| 4,172,524 A | * | 10/1979 | Holm et al. ................... | 209/524 |
| 4,800,748 A | * | 1/1989 | Fischer et al. ................ | 73/865.9 |
| 4,998,440 A | * | 3/1991 | Baumel ........................... | 73/810 |
| 5,046,368 A | | 9/1991 | Baumel | |
| 2006/0153482 A1 | * | 7/2006 | Koike et al. ................... | 384/448 |

FOREIGN PATENT DOCUMENTS

| | | |
|---|---|---|
| DE | 3321827 | 7/1984 |
| GB | 1438200 | 6/1976 |

OTHER PUBLICATIONS

Search Report for GB0814037.8 dated Nov. 28, 2008.

* cited by examiner

*Primary Examiner* — Max Noori
(74) *Attorney, Agent, or Firm* — Marshall, Gerstein & Borun LLP

(57) ABSTRACT

A method of considering the dynamic behavior of a movable member of a machine for performing a wheel fatigue test, the wheel including a disc and a rim, the method including mounting the wheel by fixing the wheel rim relative to a fixed structure of the machine, and securing the disc relative to the movable member which is movable to transmit a cyclical bending moment to the wheel, exerting a cyclical force on the movable member to generate the bending moment, at a distant position from the wheel, and while exerting the cyclical force, determining an indication of bending moment in the movable member at a first position between the wheel and the distant position, determining an indication of bending moment in the movable member at a second position between the first position and the distant position, and using the indications of bending moment at both of the first and second positions to determine an actual bending moment applied to the wheel.

12 Claims, 2 Drawing Sheets

METHOD OF CONSIDERING THE DYNAMIC BEHAVIOR OF A MOVABLE MEMBER OF A MACHINE FOR PERFORMING A WHEEL FATIGUE TEST

BACKGROUND OF THE INVENTION

This invention relates to a method of considering the dynamic behaviour of a movable member of a machine for performing a wheel fatigue test, and more particularly to a method of determining a bending moment applied to the wheel as the member moves.

Wheels typically are constituted by two main parts namely a circular rim to which in use, a tyre is mounted, and a disc by means of which the wheel is securable to a hub of a vehicle. In order to predict the service life of a wheel of a particular design, it is known to conduct a fatigue test which involves clamping the rim to a fixed structure and attaching the disc to a member which moves to apply a bending moment to the wheel. Accurate determination of the bending moment applied is required for the testing method.

DESCRIPTION OF THE PRIOR ART

Referring to FIG. 1 a typical existing machine for performing a wheel fatigue test is shown at 10. The machine 10 includes a member which in this example is a generally frusto-conical shaft 3 which carries at an upper end thereof, a simulated vehicle hub 5. At its lower end, the hub-carrying shaft 3 is coupled to a drive shaft 11 which is rotated in use, and relative to the hub-carrying shaft 3, by operation of an electric motor 7, the rotational speed of which is controllable. The motor 7 is connected to the drive shaft 11 at or towards a lower end of the drive shaft 11 remote from the simulated hub 5, by a transmission such as a belt or chain or gear train 12. The lowest end 13 of the drive shaft 11 is received in a bearing structure 14.

A lower region 15 of the drive shaft 11 is generally cylindrical. A region of the drive shaft 11 above the lower region 15, indicated at 16, has secured to the drive shaft 11, an eccentrically carried mass 8 which rotates with the drive shaft 11 to impart a cyclically varying force on the hub mounting shaft 3 as is described below.

An upper end 18 of the frusto-conical hub-carrying shaft 3, where the simulated hub is carried, is the largest diameter end, most closely to simulate the hub 5 mounting to a vehicle.

In use a wheel 2 is secured to the simulated hub 5 by the same kind of fixings by which the wheel 2 in use, would be secured to a vehicle hub. In the example, the fixings are a plurality of bolts 20 which pass through openings in the wheel disc 4, and are screwed into the simulated hub 5. Thus the disc 4 is fixed to the simulated hub 5.

The wheel rim 6 is immovably fixed relative to the fixed structure 1 by one or a plurality of clamps provided around the circumference of the rim 6, or preferably as shown, a continuous circular clamp 22 is provided which clamps the rim 6 to the fixed structure 10 around its entire periphery.

In use the motor 7 is operated to rotate the drive shaft 11. The eccentrically mounted mass 8 is rotated with the shaft 3 and originates a centrifugal force, which because of the distance between the application direction of the force i.e. the distance from where the mass 8 is secured to the shaft 3, and the hub 5 above, creates a bending moment on the disc 4 transmitted along the hub-carrying shaft 3, via the hub 5, and to the wheel. Thus the rotating eccentric mass 8 will cause the lower end of the hub-carrying shaft 3 to undergo a circular, precessional, motion, whilst the upper end of the hub-carrying shaft 3 will be restrained from movement by the rim being fixed to the fixed structure 1 so that a cyclic bending moment is applied to the wheel 2.

The machine 10 includes a strain gauge 9 which is attached to the hub-carrying shaft 3 towards the upper end of 18 of the shaft 3, the strain gauge 9 being coupled to a bridge or other suitable circuit, which provides an output to an analysing apparatus which conditions and uses the signal, to provide a determination of the bending moment applied to the wheel 2 during the test.

With existing machines such as the machine 10 described above in relation to FIG. 1, it is fundamental to the testing methodology, to determine the exact value of the applied bending moment. The machine 10 is usually calibrated while the drive shaft 11, and hence eccentric mass 8 and hub-carrying shaft 3 are static. A known force is applied to the hub-carrying shaft 3 and the deformation value measured by the strain gauge 9 is associated to the specific value of the force. On the basis of this association, bending moments are determined in dynamic conditions (when the drive shaft 12 is rotated and the lower end of the hub-carrying shaft 3 undergoes a circular, precessional movement) assuming a linear relationship between strain gauge 9 readings and bending moment.

Such a machine 10 is intended to simulate conditions the wheel 2 will experience in use when mounted on a hub of an actual vehicle, during cornering, when the wheel 2 will be subject to the greatest bending moments.

SUMMARY OF THE INVENTION

According to the invention we provide a method of considering the dynamic behaviour of a movable member of a machine for performing a wheel fatigue test, the wheel including a disc and a rim. The method includes mounting the wheel by fixing the wheel rim relative to a fixed structure of the machine, and securing the disc relative to the movable member which is movable to transmit a cyclical bending moment to the wheel. A cyclical force is exerted on the movable member to generate the bending moment, at a distant position from the wheel, and while exerting the cyclical force, determining an indication of bending moment in the movable member is determined at a first position between the wheel and the distant position, and in the movable member at a second position between the first position and the distant position. Using the indications of bending moment at both of the first and second positions an actual bending moment applied to the wheel is determined.

It has been found that the prior art methodology and machine used in wheel fatigue testing did not take into account that based on calibration under static conditions, there relationship between actual moments and sensor, e.g. strain gauge readings, is not linear. Other factors which are amplified by the dynamic behaviour of the machine, affect the relationship between the bending moment as determined from reading a strain gauge at one position along the movable member e.g. hub-carrying shaft, and actual bending moments. Such factors include for examples only, any eccentricity of the hub-carrying shaft, the stiffness of the wheel being tested, the weight of the eccentric mass and, although this is not a major contributor, the contribution to bending moment of any part of the machine beyond the position of the strain gauge on the hub-carrying shaft, such as an uppermost part of the hub-carrying shaft itself, and the simulated hub carried by the shaft.

In particular it has been found that under dynamic conditions, a displacement of a centre of gravity of the hub-carrying shaft may occur due to the flexibility of components of the machine, and which displacement is greatly influenced by the weight of the eccentrically mounted mass and the speed of rotation of the drive shaft. This can cause a second centrifugal force to be generated which is proportional to the mass of the hub-carrying shaft and applied to its barycentre, in addition to the first mentioned centrifugal force generated by the rotating eccentrically mounted mass. The actual stiffness of the wheel under test has a not insignificant effect on the flexibility of the whole system.

By using indications of bending moments at two positions spaced along the movable member, it has been found that the dynamic effects of the machine on the movable member, can be taken into consideration in determining the actual bending moment applied to the wheel.

Preferably the method includes applying a first strain gauge to a surface of the movable member at the first position, and applying a second strain gauge to the surface of the movable member at the second position and using readings from the first and second strain gauges to determine an indication of the bending moment at each of the first and second positions.

Desirably the movable member is moved to exert the cyclical force to generate the bending moment in the wheel, by generating a first force by rotating a mass which is eccentrically mounted with respect to its axis of rotation, and coupling the mass to the movable member to generate a cyclical centrifugal force to the movable member.

The method of the first aspect of the invention may involve solving the simultaneous equations for Fx:

$$M_1 = F(x-a)$$

$$M_2 = F(x-b)$$

where
$M_1$ is the indication of bending moment at the first position;
$M_2$ is the indication of bending moment at the second position;
F is an equivalent force which represents the joint contributions of a centrifugal force applied at the distant position attributable to the rotation of the eccentric mass and a centrifugal force applied at a different position due to the dynamic behaviour of the machine;
x is a distance from where the actual bending moment is applied to the wheel to where the movable member experiences force F;
a is the distance from where the actual bending moment is applied to the wheel, to the second position;
b is the distance from where the actual bending moment is applied to the wheel to the first position.

It will be appreciated that the force F is the resultant of the force which is applied by the rotating mass to move the movable member, and a resultant force due to the dynamic behaviour of the machine, and that the distance x is representative of the distance from the wheel, where the actual bending moment is applied, to where the resultant force F is applied. By using two strain gauges or other sensors to provide an indication of bending moment at the respective first and second positions, by solving the simultaneous equations a measure of Fx can be determined. It is unnecessary to determine the individual values for F and x because the measure required is of the actual bending moment Fx.

Thus from $M_1$ and $M_2$, which by calibration of the machine, are measures of the bending moments at the first and second positions, derived from the signals from the first and second sensors, and knowing the distances a and b which are fixed, $M_3$, a measure of the actual bending moment can be determined because $$M_3 = Fx = \frac{M_2 a - M_1 b}{(a-b)}$$

Preferably the movable member is, at least when in a static condition substantially vertical, and the first and second positions are substantially aligned substantially vertically. For example, where the movable member is frusto-conical, the first and second positions are preferably aligned along the cone axis and located at the conical surface of the member.

According to a second aspect of the invention we provide a method of determining a bending moment applied to a wheel whilst performing a wheel fatigue test, using a testing machine, wherein the wheel includes a disc and a rim. The method includes mounting the wheel by fixing the wheel rim relative to a fixed structure of the machine, and securing the disc relative to a movable member which is movable to transmit a cyclical bending moment to the wheel,. A cyclical force is exerted on the movable member to generate the bending moment, at a distant position from the wheel, and while exerting the cyclical force, an indication of bending moment in the movable member at a first position between the wheel and the distant position is determined, and an indication of bending moment in the movable member at a second position between the first position and the distant position is determined. Using the indications of bending moment at both of the first and second positions an actual bending moment applied to the wheel is determined.

The method of the second aspect of the invention may include any of the features of the method according to the first aspect of the invention.

According to a third aspect of the invention we provide a machine for performing a fatigue test on a wheel which includes a disc and a rim, the machine including a fixed structure to which the wheel rim is in use fixed, a movable member relative to which in use, the wheel disc is secured, the movable member being movable to transmit a cyclical bending moment to the wheel. Means are provided to exert a cyclical force on the movable member to generate the bending moment, at a distant position from the wheel. A first sensor is located at a first position between the wheel and the distant position, and a second sensor is located at a second position between the first position and the distant position. The machine includes a signal analysing apparatus.

The first and second sensors, while the cyclical force is exerted on the movable member, determine an indication of bending moment in the movable member at the respective first and second positions, each providing a signal to the signal analysing apparatus. The signal analysing device is configured to use the indications of bending moment at both of the first and second positions to determine an actual bending moment applied to the wheel.

The machine may include a simulated vehicle hub to which the wheel disc is secured by fastenings, the hub being carried at one end of the movable member.

The movable member may in use, be substantially vertical, and the first and second positions may be substantially aligned vertically. In a preferred example, the movable member is frusto-conical, and the first and second positions are aligned along the cone axis and located at the conical surface of the member.

The first and second sensors may each be strain gauges and the analysing apparatus may include a processor to determine from the signals from the first and second sensors, an indication of bending moment experienced at each of the first and second positions.

BRIEF DESCRIPTION OF THE DRAWINGS

Embodiments of the invention will now be described with reference to the accompanying drawings in which:—

DETAILED DESCRIPTION OF THE PREFERRED EMBODIMENTS

Figure 1:
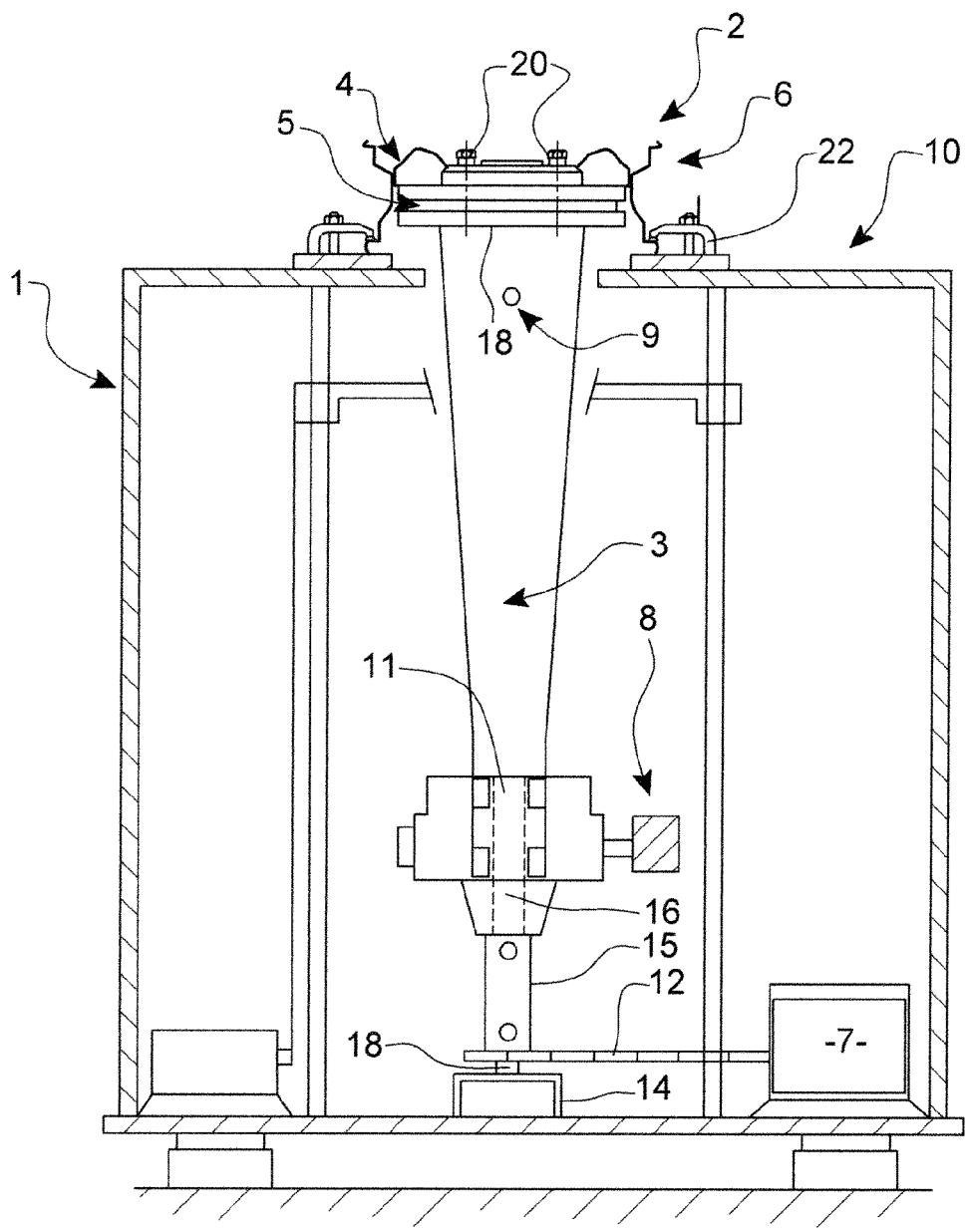
FIG. 1 is a diagrammatic illustration of a prior art machine for performing fatigue testing on wheels which is described above.

The machine 10 shown in FIG. 1 has been described above.

Figure 2:
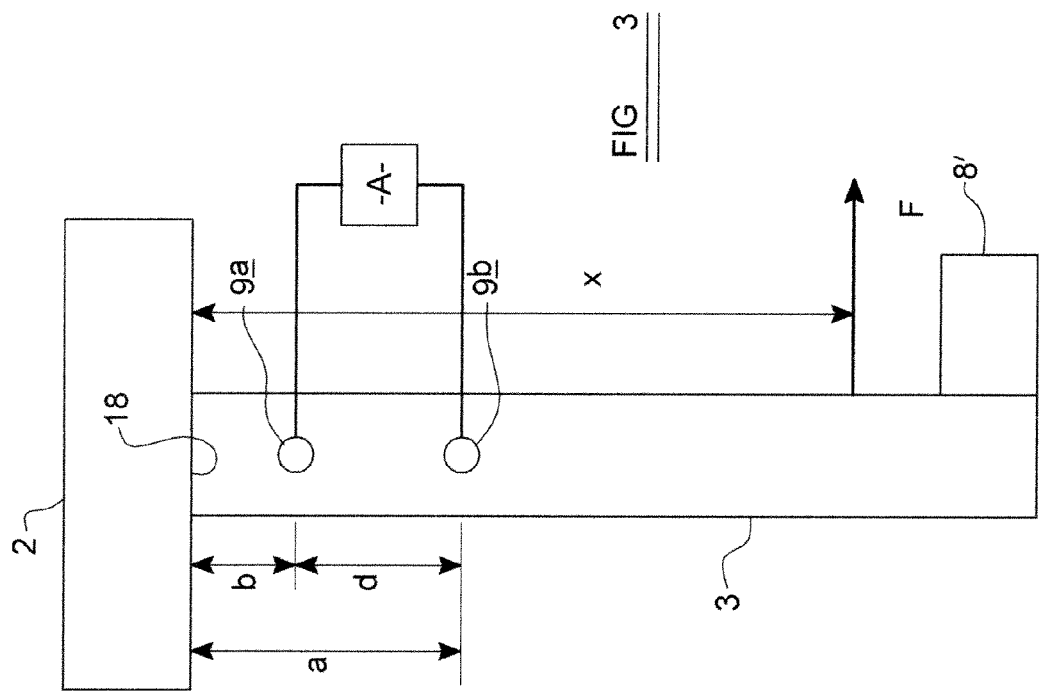
FIG. 2 is a diagram illustrating features of a machine for performing the method of the invention.

In FIG. 2 the machine 10, is shown more diagrammatically, and has been modified in accordance with the invention.

The testing machine 10 of FIG. 2, is substantially similar to that of FIG. 1, even though the configuration of the various machine 10 parts, and the wheel 2 under test are shown with less detail.

The modification to the FIG. 1 testing machine 10 which is made in FIG. 2, is the provision of first and second strain gauges 9a and 9b rather than the single strain gauge 9, with each of the two strain gauges 9a and 9b being connected operatively, to an analysing apparatus A which includes a processor, which from both of the signals from the strain gauges 9a, 9b determines more accurately the bending moment applied to the wheel 2 during testing, than is achievable with the FIG. 1 machine 10.

The first and second strain gauges 9a, 9b are substantially aligned. In the example in which the movable member, i.e. the hub-carrying shaft 3 is substantially vertical, at least when static, the two strain gauges 9a, 9b are vertically aligned axially along the hub-carrying shaft 3, located at the surface of the shaft 3. Where the shaft 3 is frusto-conical, the strain gauges 9a, 9b are located on the conical surface of the shaft 3, but still in vertical alignment along the cone axis.

The first strain gauge 9a is located at a first position with a distance a from where the bending moment is applied to the wheel 2, whilst the second strain gauge 9b is located at a second position b from where the bending moment is applied to the wheel 2. Thus the first and second strain gauges 9a, 9b are a distance d apart.

It can be seen that the eccentric weight 8 is at a distant position from the wheel 2, which is a distance h from where the bending moment is applied to the wheel 2.

In use, when rotating the eccentrically mounted weight 8, the lower end of the hub-carrying shaft 3 will be moved in a circular, precessional path thus to exert a cyclical bending moment on the wheel 2. The moment applied by the rotating weight, $M_1$ is as a result of a force $F_1$ exerted by the rotating weight 8, acting at the distance h from the wheel 2.

In addition to the force $F_1$, as is explained above, a resultant force $F_2$ will be exerted on the shaft 3 which is due to the dynamic behaviour of the machine 10 as a result of e.g. any eccentricity of the hub-carrying shaft 3, the stiffness of the wheel 2 being tested (which may be stiffer at different circumferential positions) the weight of the eccentric mass 8 and the contribution to bending moment of any part of the machine 10 beyond the position of the second strain gauge 9b on the hub-carrying shaft 3, such as the uppermost part 18 of the hub-carrying shaft 3 itself, and the simulated hub 5 carried by the shaft 3.

This force, indicated at $F_2$ in FIG. 2, which will act on the hub-carrying member 3 at an unknown position which is located at a distance c from where the bending moment is applied to the shaft 3.

Figure 3:
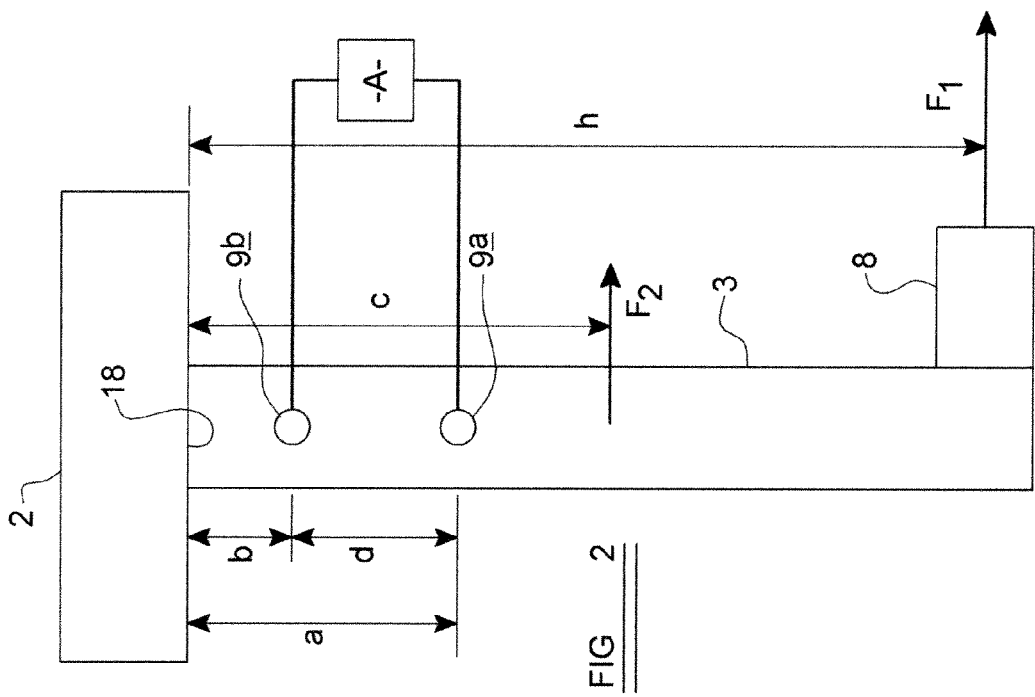
FIG. 3 is a diagram further illustrating features of a machine for performing the invention.

The actual force applied to the wheel 2, is the resultant of the forces $F_1$ and $F_2$, and is indicated at F in FIG. 3. The actual force F can be considered as the an eccentrically mounted weight 8' acting on the shaft 3, at an unknown position a distance x from where the bending moment is applied to the wheel 2.

With suitable calibration in static conditions, the signals from each of the first and second strain gauges 9a and 9b, can be processed in the analysing apparatus –A to provide determinations of bending moments experienced $M_1$, $M_2$ respectively, at the respective first and second positions. The following simultaneous equations can therefore be set up:

$$M_1 = F(x-a)$$

$$M_2 = F(x-b)$$

where $M_1$ is the bending moment at the first position determined by the analysing apparatus;

$M_2$ is the bending moment at the second position determined by the analysing apparatus;

F is the equivalent force which represents the joint contributions of the centrifugal force $F_1$ applied at the distant position a distance x from where the bending moment is applied to the wheel 2 to where the movable member 3 experiences force F, attributable to the rotation of the effective eccentric mass 8', and the centrifugal force $F_2$ due to the dynamic behaviour of the machine;

The required actual bending moment applied to the wheel 2 is $M_3$ which is given by:

$$M_3 = Fx = \frac{M_2 a - M_1 b}{(a-b)}$$

Thus by solving the simultaneous equations a measure of Fx can be determined and it is unnecessary to determine the individual values for F and x because the measure required is of the actual bending moment Fx.

The present invention thus enables a more accurate determination, taking into account the dynamic behaviour of the machine 10, of the actual bending moment applied to the wheel 2 by movable member 3 of the machine 10 during fatigue testing.

Various modification may be made without departing from the scope of the invention.

For example, the configuration of the machine 10 described may be varied, for example by providing a movable member 3 of a configuration other than frusto-conical. For example the movable member 3 may be cylindrical. The wheel 2 may be carried on the movable member 3 other than by a simulated hub 5 although the closer the machine 10 can be made to simulate actual wheel operating conditions, the more relevant the test results will be to the wheels' actual fatigue characteristic.

Although it is preferred that the wheel 2 is tested in the orientation described in which the movable member is arranged substantially upright, to avoid gravitational effects, in an alternative machine, the wheel 2 may be in another orientation, for example with the movable member 3 arranged generally horizontally.

Although current technology favours the use of strain gauges 9a and 9b to determine the bending moments at the first and second positions, in another embodiment, some other kinds of sensors may alternatively be used.

The coupling of the drive shaft 11 to the movable member 3 may be substantially rigid, or may be a resilient coupling, provided that the drive shaft 11 can rotate relative to the movable member 3. The drive shaft 11 itself, or part of it such as the lower region 15 of the drive shaft 11, may be resiliently mounted, to permit the rotating eccentric weight 8 to impart the force necessary to the movable member 3 to cause the movable member 3 to move in a circular, precessional path, at the lowest end when in the orientation of the movable member 3 in the drawings, to transmit the bending moment to the wheel 2 at the uppermost end 18 of the movable member 3. The degree of resilience of the parts of the machine 10 will be selected depending on the motion required of the movable member 3 to provide a desired bending moment in the wheel 2.

Although it is preferred that the movable member is moved as described, with the end remote from the wheel 2 moving in a circular, precessional, path, in another example, a movable member 3 to which the wheel disc 4 is secured may otherwise be moved to exert a cyclical bending moment on the wheel 2.

The invention claimed is:

1. A method of considering the dynamic behaviour of a movable member of a machine for performing a wheel fatigue test, the wheel including a disc and a rim, the method including mounting the wheel by fixing the wheel rim relative to a fixed structure of the machine, and securing the disc relative to the movable member which is movable to transmit a cyclical bending moment to the wheel, exerting a cyclical force on the movable member to generate the bending moment, at a distant position from the wheel, and while exerting the cyclical force, determining an indication of bending moment in the movable member at a first position between the wheel and the distant position, determining an indication of bending moment in the movable member at a second position between the first position and the distant position, and using the indications of bending moment at both of the first and second positions to determine an actual bending moment applied to the wheel.

2. A method according to claim 1 which includes applying a first strain gauge to a surface of the movable member at the first position, and applying a second strain gauge to the surface of the movable member at the second position and using readings from the first and second strain gauges to determine an indication of the bending moment at each of the first and second positions.

3. A method according to claim 1 which includes moving the movable member to exert the cyclical force to generate the bending moment in the wheel, by generating a force by rotating a mass which is eccentrically mounted on a drive shaft at the distant position, the drive shaft being coupled to the movable member.

4. A method according to claim 3 which includes solving the simultaneous equations for Fx:

$$M_1 = F(x-a)$$

$$M_2 + F(s-b)$$

where $M_1$ is the indication of bending moment at the first position;

$M_2$ is the indication of bending moment at the second position;

F is an equivalent force which represents the joint contributions of a centrifugal force applied at the distant position attributable to the rotation of the eccentric mass and a centrifugal force applied at a different position due to the dynamic behaviour of the machine;

x is a distance from where the actual bending moment is applied to the wheel to where the movable member experiences force F;

a is the distance from where the actual bending moment is applied to the wheel, to the second position;

b is the distance from where the bending moment is applied to the wheel to the first position.

5. A method according to claim 1 wherein the movable member is, at least when in a static condition substantially vertical, and the first and second positions are substantially aligned substantially vertically.

6. A method according to claim 1 wherein the movable member is frusto-conical, the first and second positions are aligned along the cone axis and located at the conical surface of the member.

7. A method of determining a bending moment applied to a wheel whilst performing a wheel fatigue test, using a testing machine, wherein the wheel includes a disc and a rim, the method including mounting the wheel by fixing the wheel rim relative to a fixed structure of the machine, and securing the disc relative to the movable member which is movable to transmit a cyclical bending moment to the wheel, exerting a cyclical force on the movable member to generate the bending moment, at a distant position from the wheel, and while exerting the cyclical force, determining an indication of bending moment in the movable member at a first position between the wheel and the distant position, and determining an indication of bending moment in the movable member at a second position between the first position and the distant position, and using the indications of bending moment at both of the first and second positions to determine an actual bending moment applied to the wheel.

8. A machine for performing a fatigue test on a wheel which includes a disc and a rim, the machine including a fixed structure to which the wheel rim is in use fixed, a movable member relative to which in use, the wheel disc is secured, the movable member being movable to transmit a cyclical bending moment to the wheel, means to exert a cyclical force on the movable member to generate the bending moment, at a distant position from the wheel, and a first sensor located at a first position between the wheel and the distant position, and a second sensor located at a second position between the first position and the distant position, and the machine including a signal analyzing apparatus, the first and second sensors, while the cyclical force is exerted on the movable member, determining an indication of bending moment in the movable member at the respective first and second positions, and each providing a signal to the signal analysing apparatus, and the signal analysing apparatus being configured to use the indications of bending moment at both of the first and second positions to determine an actual bending moment applied to the wheel.

9. A machine according to claim 8 wherein the machine includes a simulated vehicle hub to which the wheel disc is secured by fastenings, the 30 hub being carried at one end of the movable member.

10. A machine according to claim 8 wherein the movable member is in use, substantially vertical, and the first and second positions are substantially aligned vertically.

11. A machine according to claim 8 wherein the movable member is frusto-conical, and the first and second positions are aligned along the cone axis and located at the conical surface of the member.

12. A machine according to claim 8 wherein the first and second sensors are each strain gauges and the analysing apparatus includes a processor to determine from the signals from the first and second sensors, an indication of bending moment experienced at each of the first and second positions.

* * * * *